United States Patent
Petereit et al.

(10) Patent No.: US 7,175,857 B2
(45) Date of Patent: *Feb. 13, 2007

(54) GRANULATE OR POWDER FOR PRODUCING COATING OR BINDING AGENTS FOR MEDICAMENTS

(75) Inventors: Hans-Ulrich Petereit, Darmstadt (DE); Christian Meier, Darmstadt (DE); Erna Roth, Darmstadt (DE); Andreas Gryczke, Griesheim (DE)

(73) Assignee: Roehm GmbH & Co. KG, Darmstadt (DE)

( * ) Notice: Subject to any disclaimer, the term of this patent is extended or adjusted under 35 U.S.C. 154(b) by 511 days.

This patent is subject to a terminal disclaimer.

(21) Appl. No.: 10/489,856

(22) PCT Filed: Jul. 8, 2003

(86) PCT No.: PCT/EP03/07319

§ 371 (c)(1),
(2), (4) Date: Mar. 23, 2004

(87) PCT Pub. No.: WO2004/019918

PCT Pub. Date: Mar. 11, 2004

(65) Prior Publication Data

US 2004/0249035 A1 Dec. 9, 2004
US 2005/0197434 A9 Sep. 8, 2005

(30) Foreign Application Priority Data

Aug. 27, 2002 (DE) ................. 102 39 999

(51) Int. Cl.
*A61K 9/14* (2006.01)
*A61K 9/16* (2006.01)
(52) U.S. Cl. ..................... 424/489; 424/490
(58) Field of Classification Search ..................... None
See application file for complete search history.

(56) References Cited

U.S. PATENT DOCUMENTS

| 6,576,255 | B1 | 6/2003 | Petereit et al. |
| 6,624,210 | B1 | 9/2003 | Petereit et al. |
| 2003/0064036 | A1 | 4/2003 | Petereit et al. |
| 2004/0253314 | A1 | 12/2004 | Petereit et al. |

FOREIGN PATENT DOCUMENTS

| EP | 0164669 | 12/1985 |
| EP | 0403959 | 12/1990 |
| EP | 0727205 | 8/1996 |
| WO | WO 0005307 A1 * | 2/2000 |

OTHER PUBLICATIONS

E. Roth, et al. "Improved moisture protection with new aqueous aminomethacrylate copolymer formulations", CRS, Annual meeting 2002 in Seoul (Korea) 2002.
Hans-Ulrich Petereit, "New aspects of moisture protection and insulation of solid dosage forms with EUDRAGIT® EPO", 33st International EUDRAGIT® Workshop 2001, Sep. 27-28, 2001.

* cited by examiner

*Primary Examiner*—S. Tran
(74) *Attorney, Agent, or Firm*—Oblon, Spivak, McClelland, Maier & Neustadt, P.C.

(57) ABSTRACT

The invention relates to a process for the production of granules or powders, suitable as coating agents and binders for oral or dermal pharmaceutical forms, for cosmetics or food supplements, consisting essentially of (a) a copolymer, consisting of free radical-polymerized C1- to C4-esters of acrylic or methacrylic acid and further (meth)acrylate monomers which contain functional tertiary amino groups, (b) 3 to 25% by weight, based on (a), of an emulsifier having an HLB of at least 14, (c) 5 to 50% by weight, based on (a), of a $C_{12}$- to $C_{18}$-monocarboxylic acid or of a $C_{12}$- to $C_{18}$-hydroxyl compound, where the components (a), (b) and (c) are simultaneously or successively blended or mixed with one another, optionally with addition of a pharmaceutical active compound and/or further customary additives, fused in a heatable mixer, mixed, the melt is cooled and comminuted to give granules or powders.

11 Claims, No Drawings

GRANULATE OR POWDER FOR PRODUCING COATING OR BINDING AGENTS FOR MEDICAMENTS

The invention relates to a powder or granules for the production of coating agents and binders for pharmaceutical forms.

PRIOR ART

U.S. Pat. No. 4,705,695 describes a process for the coating of pharmaceutical formulations with an aqueous coating agent comprising a water-soluble (meth)acrylate copolymer having tertiary amino groups, and a water-insoluble, neutral polymer as a binder. The solubility of the (meth)acrylate copolymer consisting, for example, of equal proportions of methyl methacrylate and dimethylaminoethyl methacrylate, is brought about by stirring in in powder form with particle sizes below 0.25 mm in water with simultaneous addition of an acid. The binder employed is an insoluble copolymer, e.g. of methyl methacrylate and ethyl acrylate (70:30). The production of the coating solution is relatively complicated. Because of the content of acid, the coating has an unpleasant taste. Appropriate films dissolve both in artificial gastric juice and in water in less than two minutes.

WO 00/05307 describes a process for the production of a coating agent and binder for oral or dermal pharmaceutical forms consisting of (a) 35–98% by weight of a copolymer, consisting of free radical-polymerizable C1- to C4-esters of acrylic or methacrylic acid and further (meth)acrylate monomers which have functional tertiary amino groups and (b) 1–50% by weight of a plasticizer and 1–15% by weight of an emulsifier having an HLB of at least 14 where the components (a), (b) and (c) are blended with one another with or without addition of water and optionally with addition of a pharmaceutical active compound and further customary additives and the coating agent and binder is produced by fusing, casting, spreading or spraying, the copolymer (a) being incorporated in powder form with a mean particle size of 1–40 μm.

A copolymer corresponding to WO 00/05307 of methyl methacrylate, butyl methacrylate, and dimethylamino-ethyl methacrylate in the ratio 25:25:50 having a mean particle size of 15 μm is on the market under the name EUDRAGIT® EPO (Registered trademark of Röhm GmbH & Co. KG) and thus prior art.

The formulation in the defined powder form in combination with plasticizer and emulsifier makes it possible to convert the corresponding copolymers into stable aqueous solutions or dispersions without the addition of acids. There is the advantage that a bitter intrinsic taste of the coating agent which otherwise occurs can be avoided. The coating agents and binders are moreover scarcely soluble in water, but dissolve rapidly in artificial gastric juice. They are therefore suitable, in particular, for taste-isolating formulations which disintegrate rapidly in the gastric juice.

A further development of WO 00/05307 has been made known by the publications of Roth et al. ("Improved Moisture Protection with New Aqueous Aminomethacrylate Copolymer Formulations", CRS, Annual Meeting 2002 in Seoul (Korea) July 2002) and Petereit "new aspects of moisture protection and insulation of solid dosage forms with EUDRAGIT® EPO" 33th International EUDRAGIT® Workshop 2001 (Darmstadt, 27–28 Sep. 2001).

It is reported that the addition of C12–C18-fatty acids or alcohols brings about moisture protection. The addition of, for example, 10% by weight of sodium lauryl sulfate and 15% by weight of stearic acid to EUDRAGIT® EPO in dispersed form is especially recommended.

Object and Achievement

The invention originates essentially from the EUDRAGIT®EPO formulations mentioned at the outset with addition of C12–C18-fatty acids or alcohols and emulsifiers such as, for example, sodium lauryl sulfate. Coating agents and binders produced therefrom advantageously have only a low water vapor permeability (moisture protection action). The publications of Roth et al. and Petereit recommend the dispersion of the individual components present as powders under stirring conditions. The use of the pulverulent components has the disadvantage that an undesirable formation of powder dusts always accompanies it, which as a rule is undesirable in the case of the end user. It was therefore regarded as an object to make available an intermediate which can be processed easily and with markedly reduced dust development by the end user to give a coating agent and binder.

The object is achieved by a process for the production of granules or powder, suitable as a coating agent and binder for oral or dermal pharmaceutical forms, for cosmetics or food supplements, consisting essentially of (a) a copolymer, consisting of free radical-polymerized C1- to C4-esters of acrylic or methacrylic acid and further (meth)acrylate monomers which contain functional tertiary amino groups, (b) 3 to 25% by weight, based on (a), of an emulsifier having an HLB of at least 14, (c) 5 to 50% by weight, based on (a), of a $C_{12}$- to $C_{18}$-monocarboxylic acid or of a $C_{12}$- to $C_{18}$-hydroxyl compound, where the components (a), (b) and (c) are simultaneously or successively blended or mixed with one another, optionally with addition of a pharmaceutical active compound and/or further customary additives, fused in a heatable mixer, mixed, the melt is cooled and comminuted to give granules or powder.

Owing to the extrusion process of the components (a), (b) and (c), and optionally additionally added pharmaceutical active compounds and/or further customary additives, a molecular matrix obviously results which, after comminution, substantially affords dust-free processable powder or granules. The end user can easily process the granules or powder further in a customary manner. The powder or granules save the prestocking, weighing and the incorporation of many individual components, since these are already present in the specified amounts. The dust development using the powders or granules according to the invention is avoided. It is surprising that even copolymers as in component (a), which are present in powder form having a mean particle size of over 40 μm, and which in this form as a rule necessitate relatively long dispersion times, of, for example, a number of hours, can be converted in this way into a rapidly dispersible form. It is even more surprising, however, that using the present invention even granules, for example, having particle sizes of 0.5–5 mm, can be converted into a rapidly dispersible form.

CARRYING OUT THE INVENTION

Component (a)

The copolymers (a) consist essentially or completely of free radical-polymerized C1- to C4-esters of acrylic or methacrylic acid and further (meth)acrylate monomers which contain functional tertiary amino groups.

Suitable monomers having functional tertiary amino groups are listed in U.S. Pat. No. 4,705,695, column 3, line 64 to column 4, line 13. In particular, dimethylaminoethyl acrylate, 2-dimethylaminopropyl acrylate, dimethylaminopropyl methacrylate, dimethylaminobenzyl acrylate, dimethylaminobenzyl methacrylate, (3-dimethylamino-2,2-dimethly)propyl acrylate, dimethylamino-2,2-dimethly)-propyl methacrylate, (3-diethylamino-2,2-dimethly)-propyl acrylate and diethylamino-2,2-dimethly)propyl methacrylate may be mentioned. Dimethylaminoethyl methacrylate is particularly preferred.

The content of the monomers having tertiary amino groups in the copolymer can advantageously be between 30 and 70% by weight, preferably between 40 and 60% by weight. The proportions of the C1- to C4-esters of acrylic or methacrylic acid is 70–30% by weight. Methyl methacrylate, ethyl methacrylate, butyl methacrylate, methyl acrylate, ethyl acrylate, butyl acrylate may be mentioned.

A (meth)acrylate copolymer having tertiary amino groups corresponding to the component (a) can be built up, for example, from 20–30% by weight of methyl methacrylate, 20–30% by weight of butyl methacrylate and 60–40% by weight of dimethylaminoethyl methacrylate. The proportion of component (a) in the formulation is preferably 50–90% by weight.

The copolymers (a) are obtained in a manner known per se by free-radical substance, solution, bead or emulsion polymerization. They are brought into a form which is miscible dry or in the melt with the components (b) and (c) before processing by means of suitable grinding, drying or spraying processes. In particular, the granule or powder form is suitable for further processing. Suitable implements for this are familiar to the person skilled in the art, e.g. die-face pelletizers, strand pelletizers, air jet mills, pinned disk mills, fan mills. Optionally, appropriate sieving steps can be included. A suitable mill for large industrial amounts for the production of powders is, for example, an opposed jet mill (Multi No. 4200), which is operated at about 6 bar overpressure. Suitable powders can, for example, mean particle sizes of 1–40 µm (EUDRAGIT® EPO type) or between 40 µm to 50 µm. Granules can, for example, be rounded, lenticular or cylindrical with particle sizes of 0.5 to 50 mm, preferably 1 to 5 mm (EUDRAGIT® E type).

Component (b)

Emulsifiers or surfactants are surface-active substances having lyobipolar character, i.e. nonpolar, lipophilic and polar, hydrophilic centers must be present in their molecule (P.H. List, Arzneiformenlehre [Pharmaceutical form theory], Wissenschaftliche Verlagsgesellschaft mbH Stuttgart, 1982, chap. 6.2.). Depending on molecular structure, a distinction is made between ionic and nonionic emulsifiers.

The HLB is a measure of the hydrophilicity or lipophilicity of nonionic surfactants introduced in 1950 by Griffin. It can be determined experimentally by the phenol titration method according to Marszall; cf. "Parfümerie, Kosmetik" [Perfumery, cosmetics], volume 60, 1979, pp. 444–448; further references in Römpp, Chemie-Lexikon [Chemical encyclopedia], 8th ed. 1983, p. 1750. See furthermore, for example, U.S. Pat. No. 4,795,643 (Seth)).

An HLB (hydrophilic/lipophilic balance) can only be determined exactly with nonionic emulsifiers. With anionic emulsifiers, this value can be determined arithmetically, but is virtually always above or far above 14.

Emulsifiers (b) having an HLB of above 14 are understood according to the invention as meaning hydrophilic, nonionic emulsifiers having an HLB range of at least 14, and likewise hydrophilic, anionic emulsifiers and their salts which have an arithmetical HLB of above 14. Emulsifiers having HLBS of less than 14, such as, for example, glycerol monostearate can admittedly additionally also be present, but do not replace the emulsifiers (b) having HLBs of at least 14.

Suitable emulsifiers (b) are, for example, sodium lauryl sulfate and sodium cetylstearyl sulfate, sucrose stearate and polysorbate 80. The emulsifiers (b) are present in amounts of 1–25, preferably 5–10, % by weight based on component (a). Of course, the use of emulsifier mixtures is also possible.

The addition of the emulsifiers (b) to the formulation can be performed in a known manner, directly, in aqueous solution or after thermal pretreatment of the mixture.

Depending on type (lipophilic or hydrophilic) and amount added, the emulsifiers can influence the functionality of the polymer layer.

Component (c)

Component (c): 5 to 50, preferably 10 to 20, % by weight, (based on component (a)), of a $C_{12}$- to $C_{18}$-monocarboxylic acid or of a $C_{12}$- to $C_{18}$-hydroxyl compound. Component (c) is crucial for the surprisingly low water vapor permeability of the formulations.

Unbranched $C_{12}$- to $C_{18}$-monocarboxylic acid or a $C_{12}$- to $C_{18}$-hydroxyl compounds are preferred. If appropriate, branched derivatives of the substances mentioned can also be suitable.

$C_{12}$- to $C_{18}$-monocarboxylic acids are, for example, in particular, lauric acid and myristic acid. Palmitic acid and stearic acid are preferred.

$C_{12}$- to $C_{18}$-hydroxyl compound, in particular alkanols having a terminal hydroxyl group such as, for example, lauryl alcohol or stearyl alcohol.

Further Additives

Customary additives are preferably added to the formulation according to the invention during the production of the granules or powders. The additives can also additionally be added to the coating agent and binder during processing. In principle, of course, all substances employed must be toxicologically harmless and in particular be able to be used in medicaments without risk for patients.

Amounts employed and use of the customary additives in pharmaceutical coatings or coverings are familiar to the person skilled in the art. Customary additives can be, for example, mold-release agents, pigments, stabilizers, antioxidants, pore-forming agents, penetration promoters, lustering agents, aromatic substances or flavorings. They are used as processing aids and should guarantee a safe and reproducible production process and good long-term storage stability or they achieve additional advantageous properties in the pharmaceutical form. They are added to the polymer preparations before processing and can influence the permeability of the coatings, which can optionally be utilized as an additional control parameter.

Mold-release agents:

Mold-release agents as a rule have lipophilic properties and as a rule are added to the spray suspensions. They prevent agglomeration of the cores during the making into a film. Preferably, talc, Mg stearate or Ca stearate, ground silicic acid, kaolin or nonionic emulsifiers having an HLB of between 3 and 8 are employed. Customary amounts employed for mold-release agents in the coating agents and binders according to the invention are between 0.5 to 100% by weight based on the copolymer (a).

Pigments:

Pigments incompatible with the coating agent are in particular those pigments which, when they are added directly to the (meth)acrylate copolymer dispersion, e.g. by stirring in, in customary use amounts of, for example, 20 to 400% by weight based on the dry weight of the (meth) acrylate copolymer, lead to the destabilization of the dispersion, coagulation, to demixing phenomena or similarly undesirable effects. Furthermore, the pigments to be used are, of course, nontoxic and suitable for pharmaceutical purposes. For this, for example, also see: Deutsche Forschungsgemeinschaft [German research association], *Farbstoffe für Lebensmittel [Colorants for foodstuffs]*, Harald Boldt Verlag K G, Boppard (1978); Deutsche Lebensmittelrundschau 74, No. 4, p. 156 (1978); Arzneimittelfarbstoffverordnung [Pharmaceutical colorants order] AmFarbV of Aug. 25, 1980.

Pigments incompatible with the coating agent can be, for example, aluminum oxide pigments. Incompatible pigments are, for example, Orange Yellow, Cochineal Red lake, color pigments based on aluminum oxide or azo dyes, sulfonic acid dyes, Orange Yellow S (E110, C.I. 15985, FD&C Yellow 6), indigocarmine (E132, C.I. 73015, FD&C Blue 2), tartrazine (E 102, C.I. 19140, FD&C Yellow 5), Ponceau 4R (E 125, C.I. 16255, FD&C Cochineal Red A), Quinoline Yellow (E 104, C.I. 47005, FD&C Yellow 10), erythrosine (E 127, C.I. 45430, FD&C Red 3), azorubine (E 122, C.I. 14720, FD&C carmoisine), amaranth (E 123, C.I. 16185, FD&C Red 2), Brilliant Acid Green (E 142, C.I. 44090, FD&C Green S).

The E numbers of the pigments indicated refer to EU numbering. For this see also "Deutsche Forschungsgemeinschaft, Farbstoffe für Lebensmittel, Harald Boldt Verlag K G, Boppard (1978); Deutsche Lebensmittelrundschau 74, No. 4, p. 156 (1978); Arzneimittelfarbstoffverordnung [Pharmaceutical colorants order] AmFarbV of Aug. 25, 1980. The FD&C numbers refer to the registration in Food, Drugs and Cosmetics by U.S. Food and Drug Administration (FDA) described in: U.S. Food and Drug Administration, Center for Food Safety and Applied Nutrition, Office of Cosmetics and Colors: Code of Federal Regulations—Title 21 Color Additive Regulations Part 82, Listing of Certified Provisionally Listed Colors and Specifications (CFR 21 Part 82).

Plasticizers

Further additives can also be plasticizers. Customary amounts are between 0 and 50, preferably 0 to 20, in particular 0 to 10, % by weight. Particularly preferably, however, at most 5% by weight or no plasticizer is contained, since the formulations are frequently already elastic enough due to the presence of the components (c) and additional plasticizer can lead to undesirable tackiness.

Depending on type (lipophilic or hydrophilic) and amount added, plasticizers can influence the functionality of the polymer layer. By means of physical interaction with the polymer, plasticizers achieve a lowering of the glass transition temperature and promote, depending on the amount added, making into a film. Suitable substances as a rule have a molecular weight between 100 and 20,000 and contain one or more hydrophilic groups in the molecule, e.g. hydroxyl, ester or amino groups.

Examples of suitable plasticizers are alkyl citrates, glycerol esters, alkyl phthalates, alkyl sebacates, sucrose esters, sorbitan esters, diethyl sebacate, dibutyl sebacate and polyethylene glycols 200 to 12,000. Preferred plasticizers are triethyl citrate (TEC), acetyl-triethyl citrate (ATEC) and dibutyl sebacate (DBS). Esters which as a rule are liquid at room temperature, such as citrates, phthalates, sebacates or castor oil, are furthermore to be mentioned. Preferably, citric acid esters and sebacic acid esters are used.

The addition of the plasticizer to the formulation can be performed in a known manner, directly, in aqueous solution or after thermal pretreatment of the mixture. Mixtures of plasticizers can also be employed.

Processing to Give Granules or Powders

The components (a), (b) and (c) are optionally blended or mixed with one another simultaneously or successively with addition of a pharmaceutical active compound and/or further customary additives. The components are then fused in a heatable mixer, mixed and the melt is cooled and comminuted to give granules or powders.

It is possible, for example, to dry the components (a), (b) and (c), and the pharmaceutical active compound and/or further customary additives optionally present, for example to mix them with one another in a gravity mixer or in a mechanical mixer. It is also possible, however, to feed the components (a), (b) and (c), and the pharmaceutical active compound and/or further customary additives optionally present, on their own or as a component mixture, directly to a heatable mixer, e.g. an extruder, via continuously operating automatic feeders. It is also possible to meter the components (b) and (c), and the pharmaceutical active compound and/or further customary additives optionally present into the melt of the component (a) on their own or as a component mixture dry or if appropriate in the fused state.

The mixture is preferably fused in an extruder and extruded by means of an extruder, e.g. extruded at temperatures in the range from 80 to 160, preferably 100 to 150° C. It can be a single-screw or a double-screw extruder, at whose end the extrudate emerges, for example, as a melt strand. The extrudate obtained is comminuted to give granules or powder. This can be carried out, for example, by means of a hot chip granulator, an extrudate granulator and/or grinding in a mill, e.g. a pinned disk mill. The extrudate can, for example, be drawn off via a withdrawal belt and fed to an extrudate granulator, which cuts up the strand into pieces 1 to 5 mm long. In the case of granules, the mean grain size can be, for example, in the range from 0.5 to 5 mm, preferably 1 to 3 mm. Suitable powder sizes can be in the range from 1 to 500 μm, preferably 100 to 500 μm.

The Further Processing of the Powder or Granules According to the Invention

The invention accordingly relates to granules or powders which can be produced by means of extrusion and subsequent comminution of the extrudate and are suitable as a precursor which is easily dispersible in water or fusible, or as an intermediate, for a coating agent and binder for oral or dermal pharmaceutical forms.

The granules or powders can be processed further at room or elevated temperature with or without addition of water and optionally with addition of pharmaceutical active compounds and/or further customary additives which are still not contained in a manner known per se by fusing, casting, spreading, spraying or granulating to give coating agents and binders. In this process, the making into a film of the coating agent and binder is a prerequisite for the functional effect in the resulting pharmaceutical forms.

The conversion of the granules or powders into a dispersion by introduction into water and stirring at room temperature is preferred. Alternatively, higher shear forces or elevated temperatures, e.g. 50 to 70° C., can be used. Under these conditions, the dispersing time can be, for example, 45 to 120 min.

The solids content of the resulting dispersion is between 5 and 30% by weight, preferably between 10 and 20% by weight). The viscosity of the dispersion depends on the concentration of the solid. As a rule, it is under 1 Pa*s.

Two or more types of granules or powders, which in each case contain various color pigment, can be processed by means of mixing to give a coating agent and binder. This has the advantage that colored mixtures can be produced. In this way, color shades can be generated which cannot be produced using individual color pigments.

The making into a film takes place, independently of the application process, by supply of energy. This can take place by means of convection (heat), radiation (infrared or microwaves) or conduction. Water employed for application as a suspending agent evaporates here, if appropriate a vacuum can also be applied in order to accelerate the evaporation. The temperature necessary for the making into a film depends on the combination of the components employed.

Further Processing of the Powders or Granules According to the Invention for the Production of Binders:

Use as binders is carried out, for example, by spraying the aqueous polymer suspension onto active compound-free cores (nonpareils) with simultaneous addition of powdered active compounds or their mixtures. A further embodiment is the spraying on of the aqueous polymer suspension together with active compounds dissolved or suspended therein.

The granules or powders can also be processed further as binders by processing by means of wet or melt granulation.

Further Processing of the Formulation According to the Invention for the Production of Coating Agents:

The granules or powders can be used as moisture-isolating and/or as taste-isolating coating agents.

Preformed supports for the coatings are capsules, tablets, granules, pellets, crystals of regular or irregular shape. The size of granules, pellets or crystals is between 0.01 and 2.5 mm, that of tablets between 2.5 and 30.0 mm. Capsules consist of gelatin, starch or cellulose derivatives.

Powders and crystals as a rule contain 100% of the biologically active substance. Preformed carriers contain from approximately 0.1 to up to 99% of the biologically active substance or of the pharmaceutical active compound, and to 1 to 99.9% by weight of further pharmaceutical excipients.

Customary production processes are direct compression, compression of dry, moist or sintered granules, extrusion and subsequent rounding, wet or dry granulation or direct pelleting (e.g. to plates) or by binding of powders (powder layering) to active compound-free spheres (nonpareils) or active compound-containing particles.

In addition to the active compound, they can contain further pharmaceutical excipients: binders, such as cellulose and its derivatives, polyvinylpyrrolidone (PVP), humectants, disintegration promoters, lubricants, disintegrants, (meth)acrylates, starch and its derivatives, sugar solubilizers or others.

Of particular importance is the disintegration time of the cores, which influences the release of the active compound. Today, shorter disintegration times of under 5, or under 10, min are strived for in the disintegration test according to Ph. Eur. Longer disintegration times are problematic because additional coatings further delay the release of the active compound and can put the therapeutic effect in question. Today, a disintegration time of 30 min is regarded as a threshold value. Testing is carried out in water and artificial gastric juice (0.1 N HCl).

The cores employed are homogeneous or have a laminated structure. If engravings are inlaid into the surfaces, these should be covered by coatings if possible but only slightly filled in. The layer thickness of the polymer powder employed according to the invention varies greatly ahd depends on the processing procedure or the amount of additives. It is between 1 and 100 µm, preferably between 10 and 50 µm. On customary tablets, one polymer application corresponds to from 0.5 to 5% by weight.

Coated microparticles can be compressed to give disintegrating tablets according to K. Lehmann et al., Drugs made in Germany 37, 2, 53–60 (1994) and T. E. Beckert et al, International Journal of Pharmaceutics 143, (1996), 13–23, without significant influence on the function of the polymer.

The function of the polymer layer made into a film in the final pharmaceutical form can be varied:

Protection from harmful environmental influences due to moisture, gases, light etc.

Odor or taste isolation, marking by color mechanical stabilization isolation of incompatible ingredients avoidance of adherence to the mucous membranes.

temporarily delayed release of active compound pH-controlled release of active compound isolation of cores from further coatings The low viscosity of the polymer mixture in aqueous dispersions is advantageous even at high solids contents of up to 30%, since engravings on the surface of tablets are reproduced in detail.

The good protective and isolating action of the polymer mixture according to the invention with, at the same time, a small influence on tablet disintegration is particularly advantageous. Even at low polymer applications of 1% by weight, a taste isolation of more than 30 sec is already achieved. Thicker coatings with a copolymer of methyl methacrylate, butyl methacrylate and dimethylaminoethyl methacrylate in the ratio 25:25:50 (EUDRAGIT® E or EUDRAGIT® EPO) improve the taste concealment, but without prolonging the disintegration time in 0.1N HCl. The reliable covering of colored cores by coatings having a high pigment content is likewise advantageous. One particular embodiment is the embedding of a second active compound in the coating on an active compound-containing core.

Application to the Formulation According to the Invention for Production on Supports The formulation according to the invention can be applied in powder form, as a melt or in aqueous suspension by means of granulation, casting, spreading or by means of spray application. Water is used here mainly as a vehicle in order to apply thin coatings uniformly to spherical cores, e.g. by spraying. Spreading processes are moreover employed for coatings. The process employed depends mainly on the carrier chosen. Dry powders are applied by spreading or dusting, if appropriate also using electrostatic forces. The making into a film can be carried out by action of heat. For carrying out it is crucial here that uniform, continuous layers result.

For application processes according to the prior art see, for example, Bauer, Lehmann, Osterwald, Rothgang, "Überzogene Arzneiformen" [Coated pharmaceutical forms] Wissenschaftliche Verlagsgesellschaft mbH Stuttgart, chap. 7, pp. 165–196.

Properties relevant for application, tests required and specifications are listed in pharmacopeia.

Details can be taken from the customary textbooks, e.g.:
Voigt, R. (1984): Lehrbuch der pharmazeutischen Technologie [Textbook of pharmaceutical technology]; Verlag Chemie Weinheim-Beerfield Beach/Fla.-Basle.
Sucker, H., Fuchs, P., Speiser, P.: Pharmazeutische Technologie [Pharmaceutical technology]; Georg Thieme Verlag Stuttgart (1991), in particular chapters 15 and 16, pp. 626–642.
Gennaro, A.R. (Editor), Remington's Pharmaceutical Sciences, Mack Publishing Co., Easton Pa. (1985), Chapter 88, pp. 1567–1573.
List, P. H. (1982): Arzneiformenlehre [Pharmaceutical form theory], Wissenschaftliche Verlagsgesellschaft mbH, Stuttgart.

Water Vapor Permeability

While coating agents and binders according to WO 00/05307 have water vapor permeabilities measured according to DIN 53 122 in the range of 400 (g/m$^2$/d) or above, the water vapor permeabilities of the coating agents and binders produced from the powders or granules according to the invention are at most 350 (g/m$^2$/d), preferably at most 300 (g/m$^2$/d), particularly preferably at most 200 (g/m$^2$/d). In particular, the powders or granules according to the invention can in many cases also be processed further with extensive or complete relinquishment of customary plasticizers. This is advantageous, since it is always attempted to keep the number of components in pharmaceutical formulations low.

Biologically Active Substances:

The pharmaceuticals employed within the meaning of the invention are intended to be used on or in the human or animal body in order
1. to cure, to alleviate, to prevent or to recognize diseases, illnesses, bodily defects or pathological symptoms.
2. to allow the condition, the state or the functions of the body or mental states to be recognized.
3. to replace active compounds or body fluids produced by the human or animal body.
4. to ward off, to eliminate or to render harmless pathogens, parasites or exogenous substances or
5. to influence the condition, the state or the functions of the body or mental states.

Customary pharmaceuticals can be taken from the reference works, such as, for example, the Rote Liste or the Merck index.

The formulation according to the invention is suitable for the administration of fundamentally any desired pharmaceutical active compounds, which can preferably be administered in isolated or protected form, such as antidepressants, beta-receptor blockers, antidiabetics, analgesics, antiinflammatories, antirheumatics, antihypotensives, antihypertensives, psychopharmaceuticals, tranquillizers, antiemetics, muscle relaxants, glucocorticoids, agents for the treatment of ulcerative colitis or Crohn's disease, antiallergics, antibiotics, antiepileptics, anticoagulants, antimycotics, antitussives, arterio-sclerosis agents, diuretics, enzymes, enzyme inhibitors, gout agents, hormones and their inhibitors, cardiac glycosides, immunotherapeutics and cytokines, laxatives, hypolipidemics, gastrointestinal therapeutics, migraine agents, mineral preparations, otologicals, Parkinson agents, thyroid therapeutics, spasmolytics, platelet aggregation inhibitors, vitamins, cytostatics and metastasis inhibitors, phytopharmaceuticals, chemotherapeutics and amino acids.

Examples of suitable active compounds are acarbose, nonsteroidal antirheumatics, cardiac glycosides, acetylsalicylic acid, virustatics, aclarubicin, acyclovir, cisplatin, actinomycin, alpha- and betasympathomimetics, (allopurinol, alosetrone, alprostadil, prostaglandins, amantadine, ambroxole, amlodipine, methotrexate, S-aminosalicylic acid, amitriptyline, amlodipine, amoxicillin, anastrozole, atenolol, atorvastatin, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, celetoxib, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytarabine, dapiprazole, desogestrel, desonide, dihydralazine, diltiazem, ergot alkaloids, dimenhydrinate, dimethyl sulfoxide, dimeticone, dipyridamoi, domperidone and domperidan derivatives, donepzil, dopamine, doxazosine, doxorubizin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistate, peptide antibiotics, phenytoin, riluzoles, risedronate, sildenafil, topiramate, macrolide antibiotics, esomeprazole, estrogen and estrogen derivatives, gestagen and gestagen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, flunarizine, fluorouracil, fluoxetin, flurbiprofen, ibuprofen, flutamide, fluvastatin, follitropin, formoterol, fosfomicin, furosemide, fusidic acid, galantamine, gallopamil, ganciclovir, gemfibrozil, gentamicin, ginkgo, St John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrin, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferon, iodine und iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquin, meloxicam, mepindolol, meprobamate, meropenem, mesalazine, mesuximide, metamizole, metformin, methotrexate, methylphenidate, methylprednisolone, metixen, metoclopramide, metoprolol, metronidazole, mianserine, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenalin and adrenalin derivatives, norfloxacin, novamine sulfone, noscapine, nystatin, ofloxacin, olanzapine, olsalazine, omeprazole, omoconazole, ondansetron, orlistate, oseltamivir, oxaceprol, oxacillin, oxiconazole, oxymetazoline, pantoprazole, paracetamol, paroxetin, penciclovir, oral penicillins, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexol, pravastatin, prazosine, procaine, promazine, propiverine, propranolol, propyphenazone, prostaglandins, protionamide, proxyphylline, quetiapin, quinapril, quinaprilate, ramipril, ranitidine, reproterol, reserpine, ribavirin, rifampicin, risperidone, ritonavir, ropinirol, rosiglitazone, roxatidine, roxithromycin, ruscogenin, rutoside and rutoside derivatives, sabadilla, salbutamol, salmeterol, scopolamine, selegiline, sertaconazole, sertindole, sertralion, sildenafil, silicates, simvastatin, sitosterol, sotalol, spaglumic acid, sparfloxacin, spectinomycin, spiramycin, spirapril, spironolactone, stavudine, streptomycin, sucralfate, sufentanil, sulbactam, sulfonamides, sulfasalazine, sulpiride, sultamicillin, sultiam, sumatriptan, suxamethonium chloride, tacrin, tacrolimus, tadalafil, taliolol, tamoxifen, taurolidine, tazarotene, tegaserod, temazepam, teniposide, tenoxicam, terazosine, terbinafine, terbutaline, terfenadine, terlipressin, tertatolol, tetracyclines, tetryzoline, theobromine, theophylline, butizine, thiamazole, phenothiazines, thiotepa, tiagabin, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, anti6strogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpine, troxerutin, tulobuterol, tyramine, tyrothricin, urapidil, ursodeoxycholic acid, chenodeoxycholic acid, valacyclovir, valdecoxib, valproic acid, vancomycin, vardenafil, vecuronium chloride, venlafaxin, verapamil, vidarabine, vigabatrine, viloxazine, vinblastine, vincamine, vincristine, vindesine, vinorelbine, vinpocetin, viquidil, warfarin, xantinol nicotinate, xipamide, zafirlukast, zalcitabin, zanamivir, zidovudine, zolmitriptan, zolpidem, zoplicon, zotepine and the like.

The active compounds can, if desired, also be used in the form of their pharmaceutically acceptable salts or derivatives, and in the case of chiral active compounds both optically active isomers and racemates or diastereoisomer mixtures can be employed. If desired, the compositions according to the invention can also contain two or more pharmaceutical active compounds.

Examples of particularly preferred active compounds are acetylsalicylic acid, carbenoxolone, cefalotin, epinefrine, imipramine, potassium iodide, ketoprofen, levodopa, nitrazepam, nitroprusside, oxitetracycline HCl, promethazine, omeprazole or other benzimidazole derivatives and streptomycin.

Particularly preferred are moisture-sensitive pharmaceutical active compounds from the active compounds classes of the analgesics, antirheumatics, active compounds for the treatment of gastric ulcers, antibiotics, antihypotensives, antidepressants, thyroid therapeutics, Anti Parkinson active compounds, anxiolytics, peptides, phospohordiesterase inhibitors, proteins, cardiovascular agents or neuroleptics or their salts is present.

Moisture-sensitive pharmaceutical active compounds are, for example, acetylsalicylic acid, carbenoxolone, cefalotin, epinefrine, imipramine, potassium iodide, ketoprofen, levodopa, nitrazepam, nitroprusside, oxitetracycline HCl, promethazine, omeprazole or other benzimidazole derivatives, ranitidine or streptomycin or their salts.

Administration Forms:

In principle, the pharmaceutical forms described can be used directly by means of oral administration. The granules, pellets, or particles produced according to the invention can be filled into gelatin capsules, sachets or into suitable multidose containers having a metering device. They are taken in solid form or suspended in liquids. By means of compression from, optionally after admixture of further excipients, tablets which disintegrate after taking and which usually release coated subunits are obtained. Likewise conceivable is the embedding of agglomerates in polyethylene glycol or lipids for the production of suppositories or vaginal pharmaceutical forms. Coated tablets are packed in blister packs or multidose containers and removed by the patient directly before taking.

Classes of active compounds and substances which often can produce a bitter taste and can advantageously be formulated using the coating agents and binders according to the invention are, for example:

Analgesics and Antirheumatics: paracetamol, diclofenac, aceclofenac, ibuprofen, ketoprofen, flubiprofen, levacetylmethadol, oxycodone Psychopharmaceuticals: prometazine, donepezil, modafinil, nefazodone, reboxetin, sertindole, sertralin Antibiotics: erythromicyn, roxithromycin, clarithromycin, grepafloxacin, ciprofloxacin, levofloxacin, sparfloxacin, trovafloxacin, nevirapine Beta-blockers propanolol, metoprolol, bisoprolol, nebivolol Antidiabetics: metformine, miglitol, repaglinide H1 Antihistaminics: diphenhydramine, fexofenadine, mizolastine H2 Antihistaminics cimetidine, nizatidine, ticlopidine, cetridine, ranitidine, Vitamins: thiamine nitrate; Others: quinidine sulfate, amiloprilose HCl, pseudoephedrine HCl, sildenafil, topiramate, granisetrone, rebamipides, quinine HCl.

EXAMPLES

EUDRAGIT® E 100: copolymer of methyl methacrylate, butyl methacrylate, and dimethylaminoethyl methacrylate in the ratio 25:25:50

P=parts by weight=% by weight

Example 1

Production of colorless granules which can be rapidly dispersed.

15 parts (P) of stearic acid are mixed with 7 P of sodium lauryl sulfate in a suitable mixer and subsequently extruded with 100 P of EUDRAGIT® E 100 in a synchronous 18 mm double screw extruder, whose screws are provided with compounding elements, at temperatures between 105 to 140° C. with a throughput of about 1.6 kg/h. The extrudate is drawn off via a withdrawal belt and fed to an extrudate granulator, which comminutes the extrudate into pieces about 3.05 mm (0.12 inch) long. The mean diameter of the granule grains obtained is 2 mm and is dependent on the withdrawal rate of the extrudate.

15 P of the granules thus obtained can be dispersed in 100 P of purified water within 60 min at 63° C. by means of a magnetic stirrer. The film cast from this dispersion is homogeneous.

Example 2

Production of yellow granules which can be rapidly dispersed.

15 P of stearic acid are mixed with 10 P of sodium lauryl sulfate and 15 P of SICOVIT Yellow 10 (E 172) in a suitable mixer and subsequently extruded with 100 P of EUDRAGIT® E 100 in a synchronous 18 mm double screw extruder, whose screws are provided with compounding elements, at temperatures between 105 to 140° C. with a throughput of about 1.6 kg/h. The extrudate is drawn off via a withdrawal belt and fed to an extrudate granulator, which comminutes the extrudate into pieces about 3.05 mm (0.12 inch) long. The mean diameter of the granule grains obtained is 2 mm and is dependent on the withdrawal rate of the extrudate.

15 P of the granules thus obtained can be dispersed in 100 P of purified water within 60 min at 63° C. by means of a magnetic stirrer. The film cast from this dispersion is homogeneous.

Example 3

Production of blue granules which can be rapidly dispersed.

15 P of stearic acid are mixed with 10 P of sodium lauryl sulfate and 15 P of SICOPHARM indigotin lake (E 132) in a suitable mixer and subsequently extruded with 100 P of EUDRAGIT® E 100 in a synchronous 18 mm double screw extruder, whose screws are provided with compounding elements, at temperatures between 105 to 140° C. with a throughput of about 1.6 kg/h. The extrudate is drawn off via a withdrawal belt and fed to an extrudate granulator, which comminutes the extrudate into pieces about 3.05 mm (0.12 inch) long. The mean diameter of the granule grains obtained is 2 mm and is dependent on the withdrawal rate of the extrudate.

15 P of the granules thus obtained can be dispersed in 100 P of purified water within 60 min at 63° C. by means of a magnetic stirrer. The film cast from this dispersion is homogeneous.

Example 4

Production of taste-isolated quinidine sulfate tablets For the production of the spray dispersion, 532 g of completely demineralized water warmed to 63° C. are introduced. 111.72 g of the granules described in example 2 are added to the water and dispersed with stirring for about 60 min. 11.17 g of talc are added to the dispersion as a mold release agent. Using the spray dispersion obtained, 3000 g of quinidine sulfate cores (Ø 10 mm) are sprayed with a supply of warm air. The product temperature is between 25 and 33° C. The coated cores were subsequently dried on racks at 40° C. for two hours. The film coating obtained is uniform (and) of good covering power and shows its imperviousness by a taste isolation of greater than 30 min.

Example 5

Production of a dispersion from two different colored granules 7.5 P each of the granules described in examples 2 and 3 are dispersed in 100 P of purified water at 63° C. for about 60 min. The dispersion thus obtained has a homogeneous green color. The film cast from this dispersion is, after drying, likewise satisfying with a homogeneous color shade.

The invention claimed is:

1. A process for the production of granules or powders, suitable as coating agents and binders for oral or dermal pharmaceutical forms, for cosmetics or food supplements, consisting essentially of
    (a) 50 to 90 by weight, of a copolymer, consisting of free radical-polymerized C1- to C4-esters of acrylic or methacrylic acid and further (meth)acrylate monomers which contain functional tertiary amino groups, wherein the copolymer is present in granule or powder form,
    (b) 3 to 25% by weight, based on (a), of an emulsifier having an HLB of at least 14, and
    (c) 5 to 50% by weight, based on (a), of a $C_{12}$- to $C_{18}$-monocarboxylic acid or of a $C_{12}$- to $C_{18}$-hydroxyl compound,
    where the components (a), (b) and (c) are simultaneously or successively blended or mixed with one another, optionally with addition of a pharmaceutical active compound and/or further customary additives, fused in a heatable mixer, mixed, the melt is cooled and comminuted to give granules or powders wherein the coating and binding agents have a water vapor permeability of at most 300 ($g/m^2/d$) as measured according to DIN 53 122.

2. The process as claimed in claim 1, wherein characterized in that the heatable mixer employed is an extruder.

3. The process as claimed in claim 2, characterized in that a double screw extruder is employed.

4. The process as claimed in one or more of claim 2 to 3, characterized in that extrusion is carried out at temperatures in the range from 80 to 160° C.

5. Granules or powder, suitable as a readily water-dispersible or fusible precursor for a coating agent and binder for oral or dermal pharmaceutical forms, for cosmetics or food supplements, characterized in that it can be produced as claimed in one or more of claims 1 to 4.

6. The use of granules or powders as claimed in claim 5 for the production of a pharmaceutical form which is contained a moisture-sensitive pharmaceutical active compound from the active compound classes of the analgesics, antirheumatics, active compounds for the treatment of gastric ulcers, antibiotics, antihypotensives, antidepressants, thyroid therapeutics, anti Parkinson active compounds, anxiolytics, peptides, phosphordiesterase inhibitors, proteins, cardiovascular agents or neuroleptics or their salts.

7. The use as claimed in claim in claim 6, characterized in that the moisture-sensitive pharmaceutical active compound present is acetylsalicylic acid, carbenoxolone, cefatotin, epinefrine, imipramine, potassium iodide, ketoprofen, levodopa, nitrazepam, nitroprusside, oxitetracycline HCl, promethazine, omeprazole or other benzimidazole derivatives, ranitidine or streptomycin or their salts.

8. The use of the powder or granules as claimed in claim 5 as a moisture-isolating coating.

9. The use of the powder or granules as claimed in claim 5 as a taste-isolating coating for active compound-containing pharmaceutical compositions.

10. The use of the powder or granules as claimed in claim 5 as a binder by processing by means of wet or melt granulation.

11. The use of two or more types of granules or powders as claimed in claim 5, the granules or powders in each case containing a different color pigment and being processed by mixing to give a coating agent and binder.

* * * * *